United States Patent [19]
Jubin, Jr. et al.

[11] Patent Number: 5,849,937
[45] Date of Patent: Dec. 15, 1998

[54] EPOXIDATION PROCESS USING SERIALLY CONNECTED CASCADE OF FIXED BED REACTORS

[75] Inventors: John C. Jubin, Jr., West Chester; Jeffrey B. Danner, Kennett Square, both of Pa.

[73] Assignee: Arco Chemical Technology, L.P., Greenville, Del.

[21] Appl. No.: 995,239

[22] Filed: Dec. 19, 1997

[51] Int. Cl.⁶ ...................... C07D 301/12; C07D 301/19
[52] U.S. Cl. ............................... 549/529; 549/531
[58] Field of Search ..................... 549/529, 531

[56] References Cited

U.S. PATENT DOCUMENTS

| | | | |
|---|---|---|---|
| 2,271,646 | 2/1942 | Kassel | 196/49 |
| 2,322,366 | 6/1943 | Kassel | 196/49 |
| 3,829,392 | 8/1974 | Wulff | 252/430 |
| 4,367,342 | 1/1983 | Wulff et al. | 549/529 |
| 4,560,536 | 12/1985 | Tabak | 422/116 |
| 4,937,051 | 6/1990 | Graven et al. | 422/194 |
| 5,573,736 | 11/1996 | Jubin, Jr. | 422/191 |

FOREIGN PATENT DOCUMENTS 0323663  12/1988  European Pat. Off. .

OTHER PUBLICATIONS

"Shell Permit Documents for Moerdijk (Netherlands) PO/SM Plant", 12 Dec., 1996.

Yen, Yen–Chen *Propylene Oxide and Ethylene Oxide,* Report No. 2 C, Apr. 1977, Process Economics Program (Stanford Research Institute), pp. 221, 223.

Wang, Shao–Hwa *Propylene Oxide,* Report No. 2E, Aug. 1994, Process Economics Program (SRI International), pp. 6–28.

*Primary Examiner*—Ba K. Trinh
*Attorney, Agent, or Firm*—Stephen D. Harper

[57] ABSTRACT

An olefin epoxidation process is operated using a plurality of reactor vessels, each containing a fixed bed of a heterogeneous catalyst such as titania-on-silica. The reactor vessels are connected in series whereby a feedstream comprised of olefin and an active oxygen species is passed through said series of reactor vessels in contact with the heterogeneous catalyst to accomplish conversion of the olefin to the corresponding epoxide. As the activity of the catalyst in an individual reactor vessel falls to an undesirably low level, said reactor vessel is taken out of service and a replacement reactor vessel containing fresh or regenerated catalyst introduced. The replacement reactor vessel may, in alternative embodiments of the process, be the first or the last reactor vessel in said series. For example, the feedstream may first be contacted with either the most active or the least active charge of catalyst within the series of reactor vessels. Although the latter embodiment permits somewhat longer catalyst life, the former embodiment requires much smaller capacity heat exchangers. The process of this invention considerably reduces catalyst usage as compared to a conventional fixed bed epoxidation process where all of the catalyst is replaced or regenerated at the same time.

26 Claims, 2 Drawing Sheets

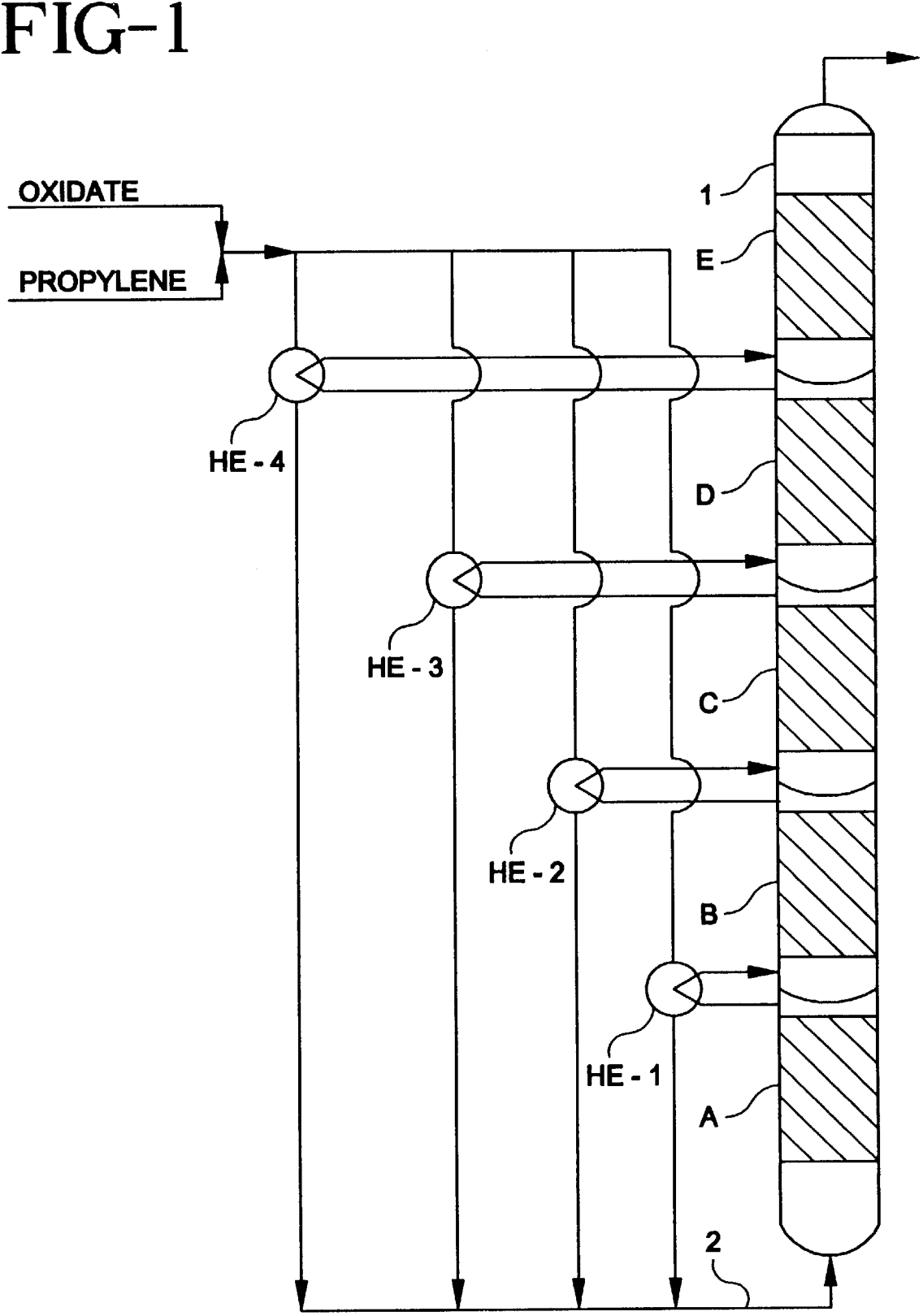

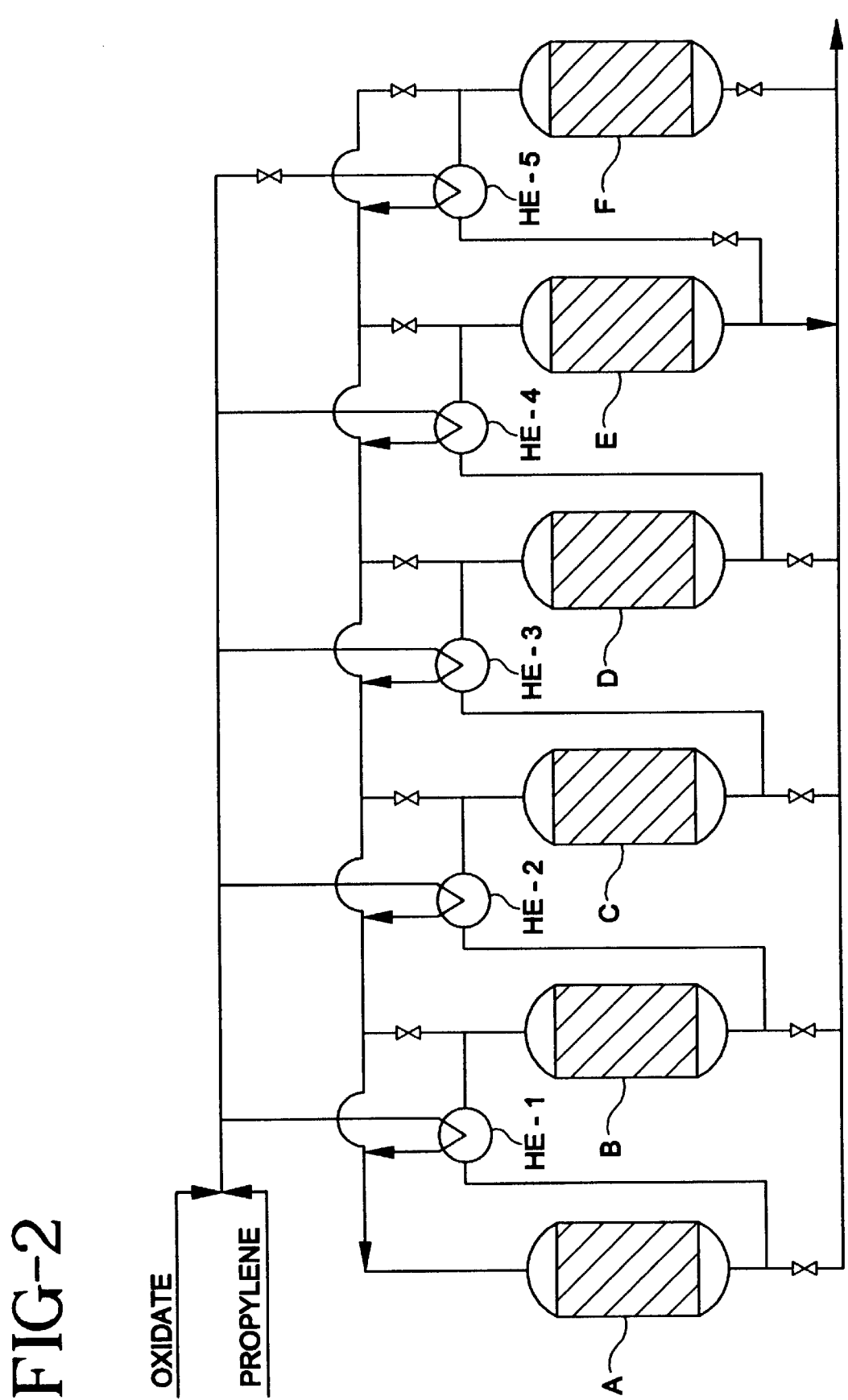

EPOXIDATION PROCESS USING SERIALLY CONNECTED CASCADE OF FIXED BED REACTORS

FIELD OF THE INVENTION

This invention provides a method of operating an epoxidation facility utilizing a heterogeneous catalyst such that the life of the catalyst may be significantly extended. More particularly, the invention pertains to a serially connected cascade of fixed bed reactors wherein individual reactors are periodically taken off-line for catalyst regeneration or replacement when catalyst activity has declined to an undesirable extent; additional reactors containing fresh catalyst are introduced into service so that the epoxidation may proceed without interruption. A feedstream containing an olefin and an active oxygen species is continually fed through the reactor cascade, with the temperature of the exothermic process being desirably controlled by means of heat exchangers so as to maintain high epoxide selectivity. In one embodiment the feedstream is contacted first with the highest activity catalyst in the series. In another embodiment, the feedstream is contacted first with the lowest activity catalyst, with a replacement reactor being introduced at the terminal position of the series.

BACKGROUND OF THE INVENTION

Over the last several decades, different types of insoluble substances have been found to be highly active and selective catalysts for transforming olefins such as propylene to epoxides such as propylene oxide using active oxygen species. One class of such catalysts includes the titanium silicalites such as TS-1 and other zeolites having titanium atoms in their framework structures which work well where the oxidant is hydrogen peroxide and the olefin is relatively small. See, for example, U.S. Pat. No. 4,833,260. When the active oxygen species is an organic hydroperoxide such as ethyl benzene hydroperoxide, the use of porous amorphous catalysts such as those commonly referred to as "titania-on-silica" is preferred. Olefin epoxidation using such catalysts is generally described, for example, in U.S. Pat. No. 4,367,342.

Although heterogeneous epoxidation catalysts exhibit high activity and selectivity when freshly prepared, gradual deactivation takes place simultaneous with epoxidation. This problem is particularly acute in a large scale continuous commercial operation where, for economic reasons, an epoxidation process must be capable of being operated over an extended period of time while maintaining high yields of epoxide. Although regeneration methods for such catalysts are known, it would be highly advantageous to develop procedures whereby the interval between regenerations is extended for as long as possible. Regeneration requires that epoxidation be interrupted for some period of time sufficient to effect catalyst reactivation, thereby reducing the effective annual capacity of a commercial plant. The deactivated catalysts could alternatively be replaced with fresh catalyst, but the same practical disadvantages will result with regeneration. Additionally, catalysts of this type tend to be relatively costly and it would be desirable to minimize the quantity of fresh catalyst which is needed to supply the plant.

SUMMARY OF THE INVENTION

This invention provides a method of operating an olefin epoxidation facility comprised of a serially connected cascade of at least two fixed bed reactors containing a heterogeneous catalyst wherein a feedstream comprised of the olefin and an active oxygen species is continually passed through said serially connected cascade and contacted as a liquid phase with the heterogeneous catalyst in each fixed bed reactor under conditions effective for conversion of the olefin to epoxide. Said method comprises removing one of the fixed bed reactors of said serially connected cascade from conversion service at such time as the heterogeneous catalyst in said fixed bed reactor has become deactivated to an undesirable extent and introducing into conversion service in said serially connected cascade an additional fixed bed reactor containing a heterogeneous catalyst having a level of epoxidation activity higher than the epoxidation activity of the heterogeneous catalyst taken out of conversion service. Generally speaking, the fixed bed reactor selected for removal from service will be the reactor having the lowest activity catalyst of any of the reactors in the cascade and will typically be the first reactor in the cascade.

In one embodiment of the invention, the first fixed bed reactor in the serially connected cascade is removed from conversion service, each remaining fixed bed reactor is advanced to a preceding serial position and the additional fixed reactor is introduced into conversion service in the terminal position of the serially connected cascade.

In another embodiment, which provides the advantage of requiring much smaller capacity heat exchangers, the additional fixed bed reactor is introduced into conversion service in the first position of the serially connected cascade.

An epoxidation facility operated in accordance with the present invention can be kept in production on a continuous basis without interruption for catalyst change-over and will be more tolerant of upsets, low activity catalyst and bed blockage than a facility containing a single reactor having a relatively large fixed bed of catalyst, which must be shut down periodically for catalyst replacement. Furthermore, the catalyst consumption of the serially connected cascade will be less than the single large fixed bed for an equivalent total reactor volume.

BRIEF DESCRIPTION OF THE DRAWINGS

FIG. 1 illustrates the conventional fixed bed epoxidation process described in more detail in Comparative Example 1. FIG. 2 illustrates a serially connected cascade of fixed bed reactors operated in accordance with the present invention as described in more detail in Examples 2 and 3.

DETAILED DESCRIPTION OF THE INVENTION

In the process of this invention, an olefin is reacted with an active oxygen species to form the corresponding epoxide. Although any ethylenically unsaturated organic compound could be used as the olefin, including branched, straight chain, cyclic, terminal or internal olefins, $C_2$–$C_6$ mono-olefins are particularly preferred. Examples of such mono-olefins include ethylene, propylene, n-butene, isobutylene, n-pentene, cyclohexene and the like. The active oxygen species may be any compound capable of functioning as a source of the oxygen atom to be transferred to the olefin during epoxidation. Particularly preferred active oxygen species include hydrogen peroxide, organic hydroperoxides, and precursors thereof. For example, hydrogen peroxide or an organic hydroperoxide may be supplied as such to the serially connected cascade or may be generated in situ during epoxidation.

It is generally preferred to operate at a molar ratio of active oxygen species:olefin in the range of from 1:1 to 1:30 (more preferably, from 1:5 to 1:20).

The hydrogen peroxide which may be utilized as the oxidizing agent may be derived from any suitable source. For example, the hydrogen peroxide may be obtained by contacting a secondary alcohol such as alpha-methyl benzyl alcohol, isopropyl alcohol, 2-butanol, or cyclohexanol with molecular oxygen under conditions effective to form an oxidant mixture comprised of secondary alcohol and hydrogen peroxide (and/or hydrogen peroxide precursors). Typically, such an oxidant mixture will also contain a ketone such as acetophenone, acetone, or cyclohexanone corresponding to the secondary alcohol (i.e., having the same carbon skeleton), minor amounts of water, and varying amounts of other active oxygen species such as organic hydroperoxides. One or more of the components of the oxidant mixture such as ketone may be removed in whole or in part prior to epoxidation. Molecular oxygen oxidation of anthrahydroquinone, alkyl-substituted anthrahydroquinones, or water-soluble anthrahydroquinone species may also be employed to generate the hydrogen peroxide.

The organic hydroperoxides usable as the active oxygen species in the epoxidation process of this invention may be any organic compound having at least one hydroperoxy functional group (—OOH). Secondary and tertiary hydroperoxides are preferred, however, owing to the higher instability and greater safety hazards associated with primary hydroperoxides. The organic hydroperoxide preferably has the general structure:

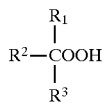

wherein $R^1$, $R^2$ and $R^3$ are the same or different and are selected from the group consisting of hydrogen, $C_1$–$C_{10}$ alkyl (e.g., methyl, ethyl, t-butyl) and $C_6$–$C_{12}$ aryl (e.g., phenyl, alkyl substituted phenyl), subject to the proviso that not more than one of $R^1$, $R^2$, or $R^3$ is hydrogen. Exemplary organic hydro-peroxides include t-butyl hydroperoxide, t-amyl hydroperoxide, cumene hydroperoxide, ethyl benzene hydroperoxide, cyclohexyl hydroperoxide, methyl cyclohexyl hydroperoxide, tetralin hydroperoxide, isobutyl benzene hydroperoxide, ethyl naphthalene hydroperoxide, and the like. Mixtures of organic hydroperoxides may also be employed.

The concentration of the active oxygen species in the feedstream introduced to the serially connected cascade of fixed bed reactors is not regarded as critical. Generally speaking, concentrations of from about 1 to 50 weight percent are suitable. The optimum concentration will depend upon the active oxygen species and heterogeneous catalyst selected for use, the liquid phase olefin concentration, and the active oxygen species: olefin molar ratio, among other factors. The liquid phase active oxygen species concentration will, of course, vary over the length of serially connected reactor cascade due to the reaction of the active oxygen species as it passes through the cascade.

The temperature, pressure, and liquid phase olefin concentration ranges selected for use with the present invention will vary somewhat depending upon the catalyst and active oxygen species employed. For example, the desirable temperature range is generally somewhat lower using a titanium silicalite catalyst and hydrogen peroxide (e.g., 40° C. to 80° C.) than when a titania-on-silica catalyst and organic hydroperoxide are utilized (e.g., 80° C. to 130° C.) although overlap of these ranges is possible.

Where the olefin is propylene and the active oxygen species is ethyl benzene hydroperoxide, it is particularly desirable to control the temperature of the feedstream as it passes through the serially connected reactor cascade such that the temperature does not exceed 125° C. Controlling the temperature in this manner will help to maintain high selectivity to propylene oxide while still permitting a high degree of hydroperoxide conversion. It will generally be desirable to achieve at least 96% (more preferably, at least 98%, most preferably, at least 99%) conversion of the active oxygen species initially present in the feedstream as it passes though the serially connected reactor cascade. It will be advantageous to operate the present process such that selectivity to epoxide based on active oxygen species converted is in excess of 90%. Where the olefin is propylene, the active oxygen species is ethyl benzene hydroperoxide, and the heterogeneous catalyst is titania-on-silica, propylene oxide selectivities greater than 98% are possible.

Organic compounds having boiling points at atmospheric pressure of from about 25° C. to 300° C. are generally preferred for use as solvents. Excess olefin may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons (e.g., ethyl benzene, cumene), halogenated hydrocarbons, and alcohols (e.g., methanol, ethanol, isopropyl alcohol, t-butyl alcohol, alpha-methyl benzyl alcohol, cyclohexanol). Where the catalyst is a titanium silicalite and the active oxygen species is hydrogen peroxide, the use of alcohols as solvents is preferred (methanol and isopropanol being particularly preferred). Such reaction systems can also tolerate substantial quantities of water without detrimental effect. If an organic hydroperoxide such as ethylbenzene hydroperoxide is utilized together with a titania-on-silica catalyst, then it is preferred that the hydrocarbon corresponding to the hydroperoxide (e.g., ethyl benzene) be used as the solvent with water being substantially excluded.

The catalyst employed in the present process may be any substance which is insoluble in the liquid phase of the epoxidation reaction mixture and capable of catalyzing the transformation of olefin to epoxide. Such catalysts are well-known in the art and may be of a crystalline (e.g., zeolitic) or amorphous character. Titanium-containing catalysts are particularly preferred for purposes of this invention.

Illustrative catalysts include titanium-containing molecular sieves comprising the class of zeolitic substances wherein titanium atoms are substituted for a portion of the silicon atoms in the lattice framework of a molecular sieve. Particularly preferred titanium-containing molecular sieves include the molecular sieves commonly referred to as "TS-1" (having an MFI topology analogous to that of the ZSM-5 aluminosilicate zeolites; see U.S. Pat. No. 4,410, 501).

Titanium-containing molecular sieves usable in the present process are sometimes variously referred to by workers in the field as "titanium silicalites", "titanosilicates", "titanium silicates", "silicon titanates" and the like.

Other suitable catalyst compositions are substances comprising an inorganic oxygen compound of silicon in chemical combination with an inorganic oxygen compound of titanium (e.g., an oxide or hydroxide of titanium). The inorganic oxygen compound of titanium is preferably combined with the oxygen compound of silicon in a high positive oxidation state, e.g., tetravalent titanium. The proportion of the inorganic oxygen compound of titanium contained in the catalyst composition can be varied, but generally the catalyst composition contains, based on total catalyst composition, at least 0.1% by weight of titanium with amounts from about 0.2% by weight to about 50% by weight being preferred and amounts from about 0.2% to about 10% by weight being most preferred.

Catalysts of this type are well-known in the art and are described, for example, in U.S. Pat. Nos. 4,367,342, 4,021,454, 3,829,392 and 3,923,843, European Patent Publication Nos. 0129814, 0345856, 0492697 and 0734764, Japanese Kokai No. 77-07,908 (Chem. Abstracts 87:135000s), PCT Application No. WO 94/23834, German Patent Document No. 3,205,648, and Castillo et al., *J. Catalysis* 161, pp. 524–529 (1996), the teachings of which are incorporated herein by reference in their entirety.

One type of such heterogeneous catalyst particularly suitable for use in the present invention is titania-on-silica (also sometimes referred to as "$TiO_2/SiO_2$"), which comprises titanium (titanium dioxide) supported on silica (silicon dioxide). The titania-on-silica may be in either silylated or nonsilylated form.

The catalyst is deployed in a serially connected cascade of fixed bed reactors. A plurality (i.e., two or more) fixed bed reactors thus are connected in series with the feedstream being introduced at one end of the first reactor in the series, passed over the bed of heterogeneous catalyst within that reactor to accomplish partial conversion of the olefin and active oxygen species to epoxide, and then withdrawn from the other end of the first reactor. The feedstream is then introduced into one end of the next reactor in the cascade, permitted to react while in contact with the fixed bed of catalyst in the next reactor, and then withdrawn from the other end of the next reactor. This procedure is repeated until the feedstream has been passed through all of the fixed bed reactors then in conversion service in the cascade. The dimensions of each reactor, the amount of catalyst charged to each reactor, and the conditions (temperature, pressure) are selected such that complete or near complete conversion of the active oxygen species is attained by the time the feedstream exits the terminal (last) reactor in the cascade while simultaneously also maintaining high selectivity to epoxide.

The heat generated from the exothermic reaction taking place between the olefin and the active oxygen species while in contact with the fixed bed of catalyst in each reactor (which typically leads to a modest increase, e.g., 1° to 25° C., in the temperature of the feedstream) may be removed by passing the feedstream exiting the reactor through a suitable heat exchanger prior to introducing the feedstream to the next fixed bed reactor in the series. The heat thereby removed may be advantageously used to preheat the feedstream being fed to the first reactor.

The number of fixed bed reactors being used in conversion service may be varied as desired to achieve an optimum balance between construction costs, operating costs (including catalyst consumption) and performance, but will typically be from 2 to 5. At least one additional fixed bed reactor containing fresh or regenerated catalyst is introduced into conversion service when needed to replace an in-service reactor containing catalyst which has become deactivated to an undesirable extent. The epoxidation facility contemplated by the present invention thus may comprise a bank containing a total of 3 to 6 fixed bed reactors operatively connected to be placed in service sequentially in selected positions within the cascade or to be taken out of service for catalyst replacement or regeneration. Normally, no more than one reactor in said bank of reactors is out of service at any given time such that continuing conversion in the remaining reactors may be maintained, thereby helping to maximize the productivity of the epoxidation facility. The reactors may be interconnected by means of piping and valves such that the flow of the feedstream through the reactor tank can be changed to achieve the desired sequence and to permit individual reactors to be removed from conversion service to allow catalyst change-over without interruption of the epoxidation taking place in the remaining reactors.

Different preferred enhancements of the present invention may be illustrated as follows using a bank of six fixed bed reactors (designated Reactor A, B, C, D, E and F). Each reactor is initially charged with freshly prepared titania-on-silica catalyst. In the first cycle of each embodiment, a feedstream containing propylene, ethyl benzene hydroperoxide and ethyl benzene is introduced first into Reactor A, passed over the fixed catalyst bed in Reactor A under conditions effective to achieve partial conversion of the propylene to propylene oxide and partial conversion of the ethyl benzene hydroperoxide to the corresponding alcohol, withdrawn from Reactor A, and then introduced into Reactor B, and thereafter serially passed through the catalyst beds of Reactors B, C, D and E in that order. Reactor F is withheld from conversion service during the first cycle. At the conclusion of the first cycle, the catalyst in Reactor A will have deactivated to a greater extent then the catalyst in the other reactors. Reactor A is then taken out of service for catalyst replacement or regeneration.

In one embodiment, Reactor B in the second cycle becomes the first reactor in the severally connected cascade (i.e., the feedstream is introduced first into Reactor B) and Reactor F containing a fresh charge of catalyst is introduced into conversion service as the last reactor in the cascade (i.e., the last reactor through which the feedstream is passed). The sequence of reactors in the cascade during the second cycle thus is B-C-D-E-F, with Reactor A being out of service. In the third cycle, Reactor B is taken out of service for catalyst replacement or regeneration and Reactor A, containing freshly prepared or regenerated catalyst, is re-introduced into conversion service in the terminal position of the cascade. During the third cycle, the sequence of reactors thus is C-D-E-F-A. This procedure, whereby the reactor containing the most deactivated catalyst (the first reactor in the series) is removed from the cascade and a reactor containing the most highly active catalyst is added at the end of the cascade, is repeated in successive cycles.

In another embodiment of the invention, Reactor F (containing fresh catalyst) is introduced into conversion service as the first reactor in the cascade at the end of the first cycle. The sequence of reactors through which the feedstream is passed during the second cycle thus will be F-B-C-D-E. At the end of the second cycle, Reactor B (which contains the least active catalyst in the serially connected cascade) is removed from service for catalyst renewal and Reactor A (now containing fresh catalyst) is added as the first reactor in the cascade. After passing through Reactor A, the feedstream is directed to the reactor containing the least active catalyst (Reactor C) and thereafter to the remaining reactors in ascending order of relative activity. The reactor sequence during the third cycle thus is A-C-D-E-F (Reactor B out of service). Likewise, the fourth cycle reactor sequence will be B-D-E-F-A (Reactor C out of service).

When the heterogeneous catalyst in the fixed bed of an individual reactor has deactivated to an undesirable extent, the reactor is taken out of service and regeneration or replacement of the catalyst carried out. While the degree of deactivation in an individual fixed bed which can be tolerated will vary depending on a number of factors, including the number of reactors in service and the minimum epoxide yield and oxidizing agent conversion deemed acceptable from a commercial perspective, the catalyst will typically not be regenerated or replaced until its activity drops below 10% of the original activity.

Regeneration of the catalyst may be conducted in accordance with any of the procedures known in the art such as calcination, solvent washing, and/or treatment with various reagents such as silyating agents, bases, oxidizing agents and the like. It is highly desirable to practice a regeneration technique where the catalyst is reactivated in place (i.e., without removal from the fixed bed reactor).

Suitable regeneration techniques are well-known in the art and are described, for example, in Japanese Laid-Open Patent Application No. 3-114536, G. Perego et al. *Proc. 7th Intern. Zeolite Confer.* 1986, Tokyo, p. 827, EP 0743094, U.S. Pat. No. 5,620,935, U.S. Ser. No. 08/770,822 (filed Dec. 20, 1996) and U.S. Ser. No. 08/770,821 (filed Dec. 20, 1996). Following regeneration or replacement of the catalyst, the fixed bed reactor may be returned to conversion service in accordance with the present invention. To maintain optimum productivity from an epoxidation facility, it will be desirable to have no more than one reactor out of service at any given time.

After withdrawal from the terminal fixed bed reactor in the cascade, the feedstream (with preferably substantially all of the active oxygen species initially present having been reacted to form epoxide) may be fractionated or otherwise treated in accordance with conventional techniques to recover the desired epoxide product. Unreacted olefin may be recycled.

EXAMPLES

COMPARATIVE EXAMPLE 1

A conventional multi-bed reactor vessel (1) is employed in which five reactor beds (A, B, C, D, E) are stacked, as illustrated in FIG. 1. Vessels of this general type are described in more detail, for example, in U.S. Pat. Nos. 2,271,646 and 2,322,366. The reactor beds are simultaneously loaded with a total of 65 Kg of a titania-on-silica heterogeneous catalyst freshly prepared as described in U.S. Pat. No. 3,829,392. The feed, comprising 286 Kg/hr ethyl benzene oxidate and 408 Kg/hr propylene, is introduced to the bottom bed of the reactor vessel through line 2 and is kept in liquid phase by operating at a pressure of 800 psia. The ethyl benzene oxidate is obtained by conventional molecular oxygen oxidation of ethyl benzene as described in U.S. Pat. No. 4,066,706 and contains about 35 weight percent ethyl benzene hydroperoxide.

At the start of the epoxidation cycle, the feed temperature is about 38° C. and the heat exchangers associated with the reactor vessel are initially by-passed. During the epoxidation cycle, the heat exchangers are used to transfer to the feed the heat generated as a result of the exothermic epoxidation reaction which takes place as the feed comes into contact with the catalyst in the fixed beds of the reactor vessels.

The temperature of the feed to the reactor vessel is gradually increased as necessary to maintain the desired level of conversion. At the end of the epoxidation cycle (303 days), the exchangers are preheating the feed to about 101° C. to maintain the temperature of the product stream exiting each catalyst bed of the reactor vessel at about 121° C., the maximum deemed desirable in this particular embodiment of the invention. Above this temperature, the selectivity and yield of propylene oxide decrease significantly. The product stream temperatures entering and exiting each of the four heat exchangers are thus as follows at the end of the cycle:

| Heat Exchanger | Enter | Exit |
| --- | --- | --- |
| HE-1 | 121° C. | 104° C. |
| HE-2 | 121° C. | 104° C. |
| HE-3 | 121° C. | 111° C. |
| HE-4 | 121° C. | 117° C. |

When the ethyl benzene hydroperoxide conversion drops below 99% and all catalyst beds are operating at 121° C. outlet, the reactor vessel is shut down in order to replace all of the beds with fresh catalyst. The used catalyst is either sent to waste disposal or regenerated for use in a future epoxidation cycle.

EXAMPLE 2

In accordance with the present invention, a bank of six separate reactor vessels (A, B, C, D, E, F) is configured as shown in FIG. 2. Only five of the reactor vessels are serially connected by means of piping and in use in conversion service at any given time. FIG. 2 shows the reactor bank during a given epoxidation cycle wherein the feedstream is fed first through Reactor A, then Reactor B, then Reactor C, then Reactor D, and finally Reactor E, with Reactor F being held out of service. Each reactor vessel contains a fixed bed comprised of 13 Kg of titania-on-silica catalyst. The reactor vessels are valved off to permit shutting down one vessel at a time for replacement of the catalyst bed. The feed composition and rate are identical to those utilized in Comparative Example 1. The inlet temperature of the feedstream introduced into each catalyst bed is controlled using the heat exchangers (HE-1, HE-2, HE-3, HE-4) such that the outlet temperature does not exceed 121° C. That is, the liquid stream withdrawn from one reactor vessel is cooled to the desired extent using a heat exchanger (thereby heating the feed stream entering the first reactor vessel) before being passed into the next reactor vessel in the series where the temperature of the liquid stream will again be increased as a result of the exothermic epoxidation taking place in the catalyst bed. At the end of the epoxidation cycle illustrated in FIG. 1, for example, the temperature of the feedstream entering the Reactor A will be about 101° C. and the temperature of the product streams entering and exiting each of the four heat exchangers in service will be as follows:

| Heat Exchanger | Enter | Exit |
| --- | --- | --- |
| HE-1 | 121° C. | 104° C. |
| HE-2 | 121° C. | 107° C. |
| HE-3 | 121° C. | 110° C. |
| HE-4 | 121° C. | 116° C. |

At the end of the epoxidation cycle, when overall conversion of the ethyl benzene hydroperoxide falls below 99% and when all five in-service catalyst beds are being operated at an outlet temperature of 121° C., the first reactor vessel in the series (Reactor A), which contains the least active catalyst in the series, is removed from service in order to replace the catalyst bed with fresh or regenerated catalyst. The deactivated catalyst may, of course, also be regenerated in situ (i.e., while still in the reactor vessel). The spare reactor vessel containing unused catalyst (Reactor F) is then placed in service as the last reactor vessel in said series. The reactor sequence during the next epoxidation cycle thus is B-C-D-E-F.

EXAMPLE 3

In this example, the epoxidation process is operated identically to the procedure described in Example 2 except that at the end of the epoxidation cycle, the first reactor vessel in the series (Reactor A) is removed from service and replaced with the spare reactor vessel containing fresh catalyst (Reactor F). As a result, the feedstream is first introduced into the reactor vessel containing the highest activity catalyst in the series of reactor vessels, rather than the reactor vessel containing the catalyst of lowest activity as in Example 2. During the next epoxidation cycle, the reactor sequence thus will be F-B-C-D-E. In subsequent cycles, the reactor containing the least active catalyst is again removed from service and the feedstream first passed through the replacement reactor having the most active catalyst in the series and thereafter through the remaining in-service reactors in ascending order of catalyst activity. During the third cycle, for example, the reactor sequence will be A-C-D-E-F, with Reactor B out of service. Somewhat shorter catalyst life is observed than in Example 2, but the exchanger surface required is reduced significantly as compared to Example 2. That is, at the end of the epoxidation cycle in Example 2, the feed entering the first reactor vessel must be heated to 101° C. in order to achieve a temperature of 121° C. in the outlet from the first reactor vessel. This requires approximately the same exchanger surface as in Comparative Example 1. The process illustrated in Example 3 does not need as large an exchanger surface since much of the temperature increase is obtained by the greater exotherm attributed to the presence of relatively fresh, highly active catalyst in the first reactor vessel of Example 3. The temperatures of the feedstream entering and exiting each of the four in-service heat exchangers at the end of the first epoxidation cycle will be as follows:

| Heat Exchanger | Enter | Exit |
| --- | --- | --- |
| HE-1 | 121° C. | 112° C. |
| HE-2 | 121° C. | 114° C. |
| HE-3 | 121° C. | 117° C. |
| HE-4 | 121° C. | 119° C. |

Table 1 compares the operating conditions for examples 1–3. The major advantage of the presently claimed invention, as illustrated by Examples 2 and 3, as compared to the conventional process described in Comparative Example 1 is reduced catalyst consumption.

TABLE 1

| Example | 1 | 2 | 3 |
| --- | --- | --- | --- |
| Relative Catalyst Activity at End of Cycle | | | |
| Bed 1 | 2.6 | 2.5 | 22.5 |
| 2 | 3.4 | 2.9 | 2.8 |
| 3 | 6 | 3.7 | 3.3 |
| 4 | 8 | 6.2 | 4.4 |
| 5 | 10 | 18 | 7.8 |
| % EBHP Conversion at End of Cycle | | | |
| Bed 1 | 28 | 29 | 66 |
| 2 | 25 | 25 | 14 |
| 3 | 24 | 20 | 10 |
| 4 | 15 | 16 | 6 |
| 5 | 7 | 9 | 3 |
| Reactor Change Cycle, Days | 303 | 666 | 570 |

TABLE 1-continued

| Example | 1 | 2 | 3 |
| --- | --- | --- | --- |
| Catalyst Life, Days | 303 | 133 | 114 |
| Kg Catalyst in Operation/ Kg per Hour Oxidate Fed | 0.10 | 0.10 | 0.10 |
| Kg Catalyst Consumed/ Kg Oxidate Feed × $10^{-5}$ | 1.4 | 0.64 | 0.77 |
| Exchanger Surface $m^2$/ Kg per Hour Oxidate Fed | 0.026 | 0.025 | 0.0086 |

We claim:

1. A method of operating an olefin epoxidation facility comprised of a serially connected cascade of at least two fixed bed reactors each containing a heterogeneous catalyst wherein a feedstream comprised of the olefin and an active oxygen species is continually passed through said serially connected cascade and contacted as a liquid phase with the heterogeneous catalyst in each fixed bed reactor under conditions effective for conversion for the olefin to epoxide, said method comprising:

(a) removing one of the fixed bed reactors of said serially connected cascade from conversion service at such time as the heterogeneous catalyst in said fixed bed reactor has become deactivated to an undesirable extent; and (b) introducing into conversion service in said serially connected cascade an additional fixed bed reactor containing a heterogeneous catalyst having a level of epoxidation activity higher than the epoxidation activity of the heterogeneous catalyst taken out of conversion service in step (a).

2. The method of claim 1 wherein the fixed bed reactor taken out of conversion service in step (a) contains heterogeneous catalyst having an activity lower than that of the heterogeneous catalyst in any of the other fixed bed reactors in the serially connected cascade.

3. The method of claim 1 wherein the fixed bed reactor taken out of conversion service in step (a) is the first fixed bed reactor in said serially connected cascade.

4. The method of claim 1 wherein the additional fixed bed reactor in step (b) is introduced into conversion service in the terminal position of said serially connected cascade.

5. The method of claim 1 wherein the additional fixed bed reactor in step (b) is introduced into conversion service in the first position of said serially connected cascade.

6. The method of claim 1 wherein said serially connected cascade consists of three to five fixed bed reactors in conversion service.

7. The method of claim 1 wherein the olefin is a $C_2$–$C_6$ monoolefin.

8. The method of claim 1 wherein the active oxygen species is selected from the group consisting of organic hydroperoxides and hydrogen peroxide.

9. The method of claim 1 wherein the heterogeneous catalyst is selected from the group consisting of titanium zeolites and titania-on-silica.

10. The method of claim 1 wherein the heterogeneous catalyst in the fixed bed reactor removed from conversion service is regenerated and said fixed bed reactor is thereafter returned to conversion service in said serially connected cascade.

11. A method of operating a propylene epoxidation facility comprised of a serially connected cascade of from 3 to 5 fixed bed reactors each containing titania-on-silica catalyst wherein a feedstream comprised of propylene and an organic hydroperoxide is continuously passed through said serially connected cascade and contacted as a liquid phase with the titania-on-silica catalyst in each fixed bed reactor under conditions effective for conversion of the propylene to propylene oxide, said method comprising:

(a) removing the first fixed bed reactor of said serially connected cascade from conversion service at such time as the titania-on-silica catalyst in said first fixed bed reactor has become deactivated to an undesirable extent;

(b) advancing each remaining fixed bed reactor of said serially connected cascade to a preceding serial position; and (c) introducing into conversion service in the terminal position of said serially connected cascade an additional fixed bed reactor containing a titania-on-silica catalyst having a desirably high level of epoxidation activity.

12. The method of claim 11 wherein the organic hydroperoxide is ethyl benzene hydroperoxide.

13. The method of claim 11 wherein the titania-on-silica catalyst in the fixed bed reactor removed from conversion service is regenerated and said fixed bed reactor is thereafter returned to conversion service in the terminal position of said serially connected cascade.

14. The method of claim 11 wherein at least 96% conversion of the organic hydroperoxide is accomplished.

15. The method of claim 11 wherein step (a) is performed when the activity of the titania-on-silica catalyst in the first fixed bed reactor has declined to a value of less than 10% of the initial activity.

16. The method of claim 11 wherein the feedstream is maintained at a temperature not greater than 125° within the serially connected cascade.

17. A method of operating a propylene epoxidation facility comprised of a serially connected cascade of from 3 to 5 fixed bed reactors each containing a titania-on-silica catalyst wherein a feedstream comprised of propylene and an organic hydroperoxide is continuously passed through said serially connected cascade and contacted as a liquid phase with the titania-on-silica catalyst in each fixed bed reactor under conditions effective for conversion of the propylene to propylene oxide, said method comprising:

(a) removing from conversion service a fixed bed reactor of said serially connected cascade at such time as the titania-on-silica catalyst in said fixed bed reactor has become deactivated to an undesirable extent, wherein the titania-on-silica catalyst in the fixed bed reactor selected for removal has an activity lower than the activity of the titania-on-silica catalyst in any of the other fixed bed reactors; and (b) introducing into conversion service in the first position of said serially connected cascade an additional fixed bed reactor containing a titania-on-silica catalyst having a desirably high level of epoxidation activity.

18. The method of claim 17 wherein the organic hydroperoxide is ethyl benzene hydroperoxide.

19. The method of claim 17 wherein the titania-on-silica catalyst in the fixed bed reactor removed from conversion service is regenerated and said fixed bed reactor is thereafter returned to conversion service in the first position of said serially connected cascade.

20. The method of claim 17 wherein the fixed bed reactor removed from conversion service is in the second position of said serially connected cascade.

21. The method of claim 17 wherein at least 98% conversion of the organic hydroperoxide is accomplished.

22. The method of claim 17 wherein the feedstream exiting each fixed bed reactor is cooled by means of a heat exchanger prior to introducing the feedstream into the next fixed bed reactor.

23. The method of claim 22 wherein the feedstream introduced into the first fixed bed reactor is heated using said heat exchanger.

24. The method of claim 17 wherein step (a) is performed when the activity of the titania-on-silica catalyst in the fixed bed reactor selected for removal from conversion service has declined to a value of less than 10% of the initial activity.

25. The method of claim 17 wherein the feedstream is maintained at a temperature not greater than 125° C. within the serially connected cascade.

26. The method of claim 17 wherein the feedstream exiting the additional fixed bed reactor introduced into conversion service in step (b) is thereafter passed through the remaining fixed bed reactors in conversion service in ascending order of catalyst activity.

* * * * *